United States Patent
Chun

Patent Number: 5,985,021
Date of Patent: Nov. 16, 1999

[54] PROCESS FOR MANUFACTURING A COMPOSITION USEFUL AS SOAP OR COSMETIC

[75] Inventor: Kyung-Ok Chun, Pusan-si, Rep. of Korea

[73] Assignee: Zion Synthetic Fiber Co., Ltd., Kijang-kun, Rep. of Korea

[21] Appl. No.: 09/012,383

[22] Filed: Jan. 23, 1998

Related U.S. Application Data

[63] Continuation-in-part of application No. 08/846,524, Apr. 29, 1997, abandoned.

[51] Int. Cl.$^6$ .................................................. C04B 14/04
[52] U.S. Cl. .............................. 106/484; 424/63; 424/65; 424/401; 252/367.1; D28/8.1
[58] Field of Search ............................... 424/63, 65, 401; 252/367.1; 106/484; D28/8.1

[56] References Cited

U.S. PATENT DOCUMENTS 4,857,306   8/1989   Roller ........................................ 424/63

OTHER PUBLICATIONS

"Cosmetic Containing Germanium", JP357126408A, Aug. 6, 1982.
"Cosmetic Made with Beeswax", JP357154115A, Sep. 22, 1982.
"Cosmetic", JP360190704A, Sep. 28, 1985.
"Cosmetic", JP361109706A, May 28, 1986.
"Cosmetic", JP363115807A, May 20, 1988.
"Pack Composition", JP401313411A, Dec. 18, 1989.
"Soap", JP407179895A, Jul. 18, 1995.
"Ultraviolet Ray–Absorbing Powder", JP407330334A, Dec. 19, 1995.

Primary Examiner—Paul Marcantoni
Attorney, Agent, or Firm—Skjerven, Morrill, MacPherson, Franklin & Friel; Alan H. MacPherson

[57] ABSTRACT

A process for manufacturing a composition useful as a soap or cosmetic comprising: pulverizing sillimanite of about 50 weight percent, zeolite of about 5 weight percent, topaz of about 20 weight percent, trona of about 5 weight percent and hematite of about 20 weight percent as the first step to about 325 mesh; putting the pulverized ingredients of the composition into an internal furnace of zeolite; placing kaolinite between the inner surface of the electric heating plate and the outer surface of the internal furnace; heating for about nine days at about 1500° C. by means of the electric heating plate; pulverizing again the ingredients of the composition having had thermal deformation from the internal furnace to at least 900 mesh; filtering the ingredients of the composition with water through a sieve of 900 mesh; precipitating for about three days said filtered solution; and drying the precipitate.

8 Claims, 2 Drawing Sheets

PROCESS FOR MANUFACTURING A COMPOSITION USEFUL AS SOAP OR COSMETIC

CROSS-REFERENCE TO RELATED APPLICATION

This is a continuation-in-part of U.S. Ser. No. 08/846,524, filed Apr. 29, 1997, now abandoned.

BACKGROUND OF THE INVENTION

1. Field of the Invention

The present invention relates to a process for manufacturing a composition useful as soap or cosmetic that emits lots of far infrared rays and negative ion.

2. Description of the Related Art

Nowadays, the industry of cosmetics has been highly developed and cosmetics for a man, woman and special purpose were produced. The cosmetics are applied not only to face but also to each region of the human body so that various nutrients and pharmacological ingredients contained in the cosmetics can be absorbed through the skin. Namely, the cosmetics are used to achieve useful effects for the human body.

The cosmetics intend to maintain the elastic skin and add to the beauty. Also, the cosmetics are used to achieve the user's incidental effects for emitting fragrance by mixing various perfumeries to the cosmetics. However, there were no cosmetics that could be health promoting for the human body. It is customary for women not to use the cosmetics when they are in poor condition.

BRIEF SUMMARY OF THE INVENTION

An object of the present invention is to provide a process for manufacturing a composition useful as a soap or cosmetic which not only has the unique functions of the conventional cosmetics such as maintenance effects of the elastic skin and moisturization effects, but also emits lots of far infrared rays and negative ion very health-promoting for the human body.

In general, infrared rays refer to a sort of electromagnetic wave having the wavelength range of 0.76–1000 micron ($\mu$). Near infrared rays have the wavelength of 0.76–1.5 micron, intermediate infrared rays have the wavelength of 1.5–5.6 micron and far infrared rays have the wavelength of 5.6–1000 micron.

Far infrared rays are used for various purposes such as heating, drying, ripening, nurturing and alleviation of pain. It is also known that application of the far infrared rays to the human body provides the perspiration operation that secretes lots of sweat and the operation for alleviation of pain. In addition, since the announcement of a clinical test that reveals good effects for the biological rhythm of the human body, there are many trials for using the far infrared rays desirably in the health industry or the food industry. As a consequence, a variety of goods using the far infrared rays are produced in large quantities and sold in the market, nowadays. For example, a sauna using far infrared rays can improve the perspiration operation of the human body with the lower temperature than that of a steam sauna. In other words, in case of a steam sauna, steam of high temperature (about 70–80(°C.) is being supplied in a sauna room, and thus users are unable to endure for a long time within the sauna room. However, the far infrared rays sauna has the higher perspiration operation than that of the steam sauna, even with the inner temperature of about 40° C. This explains the phenomena that the far infrared rays are absorbed in the human body and a self-generation is caused by means of the resonance operation of water particle within the human body.

It is a known fact that negative ion is opposite to positive ion. With reference to the human body, the theory which Mr. Bert Sakmann and Mr. E. Necher jointly studied and expressed and consequently won the prize for Nobel Physiology and Medical Science Award in 1991, reveals that a disease structure can be detected through the movement of negative ion within the cell. Namely, in the event that the human body having neutral has much positive ion due to external or internal effects, interest concerning negative ion with intent to fill up the depleted negative ion by using food or life environmental device is at its high pitch.

Applying properly negative ion to the human body having much positive ion, it is known that an autonomic nerve adjusting operation, purification operation of the blood, cell revival operation and resistance improvement operation of the cell effect.

Various ions in the atmosphere vary according to the weather condition. When a low atmospheric pressure such as a line of discontinuity and a cold front passes, positive ion increases, and with these effects, negative ion within the human body decreases and the positive ion increases thereby the occurrence rate of the disease such as neuralgia, cerebral apoplexy and asthma increases.

The conventional product emitting far infrared rays by using the material having the brand name of "BIO CERAMIC" was sold in the market. In such product, the specific functions such as the antibacterial effects, prevention of decoloration, deodorization, etc., are maximized by mixing the composition having the specific function to the ceramic material or applying chemical substance thereto. The product is supplied in the form of powder, particle or liquid phase.

However, the conventional far infrared rays emitting material (product) had the drawbacks that only the far infrared rays were emitted or emitting quantity of the far infrared rays was not sufficient. Also, as such material contains the various chemical substances, it had the drawbacks which users who wish to avoid the chemical substance cannot easily use the cosmetics.

A composition according to the present invention comprises only natural mineral entirely excluding chemical substance and emits the large quantity of negative ion and far infrared rays.

DETAILED DESCRIPTION OF THE INVENTION

Hereinafter, desirable examples of the present invention will be described with reference to the accompanying drawings.

Figure 1:
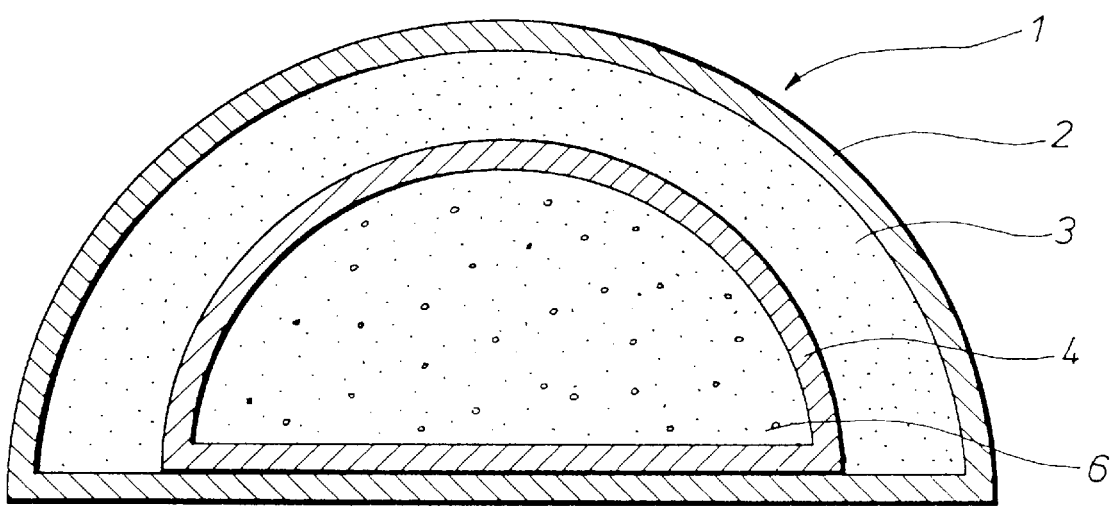
FIG. 1 is a schematic view illustrating a furnace for manufacturing a composition useful as a soap or cosmetic according to the present invention.

Referring to FIG. 1, a furnace 1 for manufacturing a composition useful as soap or cosmetic comprises an electric heating plate 2 and an internal furnace 4 made of zeolite.

The electric heating plate 2 is heated with gas or the other fuel.

Sillimanite of about 50 weight percent, zeolite of about 5 weight percent, topaz of about 20 weight percent, trona of about 5 weight percent and hematite of about 20 weight percent are initially pulverized to about 325 mesh by using a normal pulverizer, and then put into the internal furnace 4.

After placing kaolinite 3 between the inner surface of the electric heating plate 2 and the external surface of the internal furnace 4, it is heated through the electric heating plate 2 for about nine days at about 1500° C. An intense heat causes thermal deformation to such five kinds of mineral ingredients within the internal furnace 4 and consequently, heavy metals harmful to the human body are burnt out, and it becomes a lump of form which has the main ingredients having several kinds of natural mineral. After the kaolinite is burnt, a slow cooling is conducted.

Figure 2:
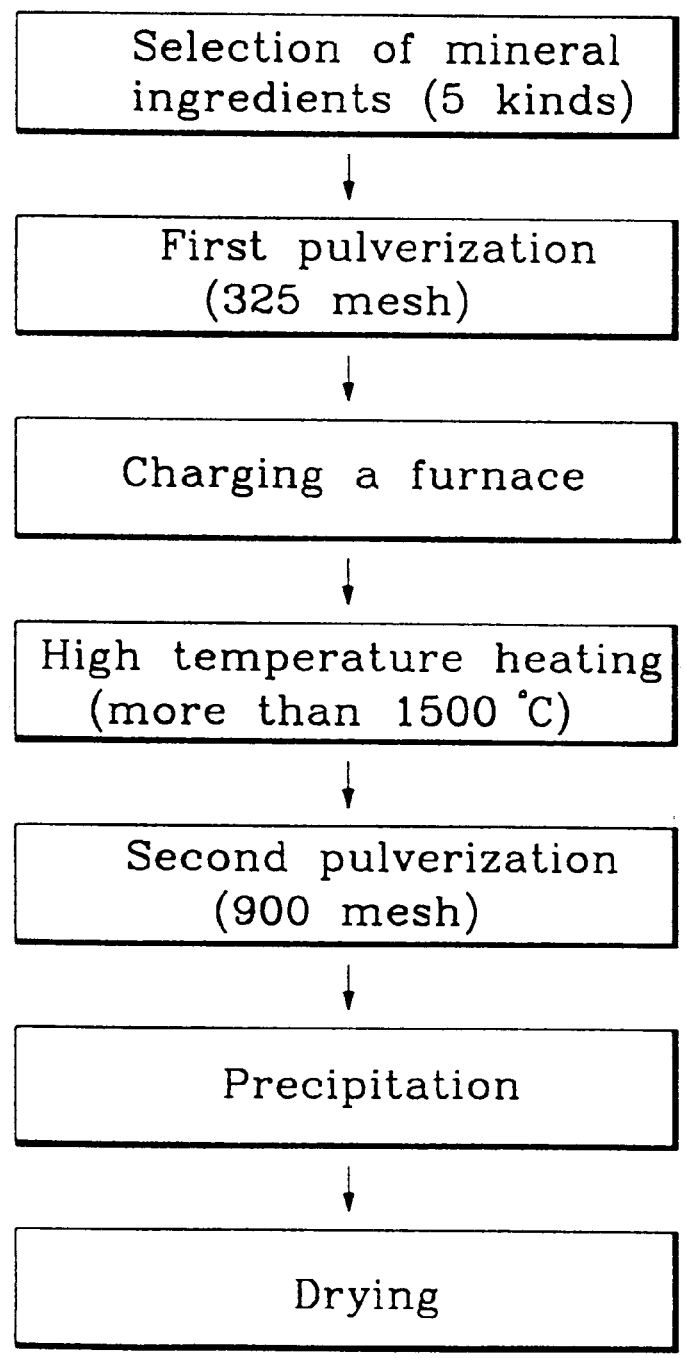
FIG. 2 is a block diagram illustrating the manufacturing progress of the composition useful as a soap or cosmetic according to the present invention.

As shown in FIG. 2, such lump is secondly pulverized again fine to at least 900 mesh. The pulverized stone ingredients are put in a sieve of 900 mesh and filtered by passing water therethrough. By precipitating the filtered water for about three days at the normal temperature, the precipitate is obtained and then dried so as to obtain the minute powder form of the composition.

The ingredients of the composition according to the present invention emit far infrared rays and negative ion that are very health promoting for the human body. The ingredients of the composition according to the present invention has more than 99.0% of far infrared rays radiation ratio having the wavelength of 9–14 micron at 37° C. and emits more than six hundred thousand number of negative ion per 1 kg of the ingredient and the calorific value of oxygen is 560 Kcal. With reference to the method of examination herein, the far infrared rays were measured by applying KS.A 5302-91 ("KS" designates a "Korean Standard" analysis); negative ion was measured by applying Negative Ion Measuring Equipment Model No. MDK-01C of a Company, Messrs. Schomandi in Germany and the calorific value of oxygen were measured by applying KS.E 3707-90.

The aforesaid ingredient has the pH of 7.4–7.9.

The ingredient of the composition according to the present invention is mixed with the raw material of the existing cosmetics in an appropriate ratio for use. The composition according to the present invention does not have a chemical response to the raw material of other cosmetics and is a minute powder without a color.

A composition useful as a soap or cosmetic according to the present invention is one emitting a large quantity of far infrared rays and negative ion. It is a useful invention having excellent effects on the skin by adding a small quantity of the composition to cosmetics and especially to toilet soap, cold cream, lotion, etc.

What is claimed is:

1. A process for manufacturing a composition useful as a soap or cosmetic comprising:

pulverizing sillimanite of 50 weight percent, zeolite of 5 weight percent, topaz of 20 weight percent, trona of 5 weight percent and hematite of 20 weight percent to about 325 mesh;

heating the pulverized composition of ingredients to thermally deform the ingredients;

pulverizing the thermally deformed ingredients to at least 900 mesh;

filtering the ingredients of the composition with a liquid through a sieve of 900 mesh; and precipitating said filtered composition.

2. The process of claim 1, wherein heating the pulverized composition includes heating the composition in an internal furnace of zeolite.

3. The process of claim 2, further comprising placing kaolinite between an inner surface of an electric heating plate and an outer surface of the internal furnace.

4. The process of claim 1, wherein the pulverized composition is heated at a temperature of approximately 1500° C.

5. The process of claim 4, wherein the pulverized composition is heated for approximately nine days.

6. The process of claim 1, wherein the liquid for filtering the ingredients of the composition comprises water.

7. The process of claim 1, wherein the filtered composition is precipitated for approximately three days.

8. The process of claim 1, further comprising drying the precipitate.

* * * * *